United States Patent [19]

Underwood

[11] 4,027,021
[45] May 31, 1977

[54] INTERFERON INDUCTION
[75] Inventor: Gerald E. Underwood, Charlestown Township, Kalamazoo County, Mich.
[73] Assignee: The Upjohn Company, Kalamazoo, Mich.
[22] Filed: Oct. 16, 1975
[21] Appl. No.: 623,185

Related U.S. Application Data
[63] Continuation-in-part of Ser. No. 500,052, Aug. 23, 1974, abandoned.
[52] U.S. Cl. .......................... 424/248.56; 424/267; 424/311; 424/312; 424/324; 424/330
[51] Int. Cl.² ............ A61K 31/535; A61K 31/445; A61K 31/135
[58] Field of Search .......... 424/248, 324, 330, 267, 424/312, 311, 248.56
[56] References Cited
FOREIGN PATENTS OR APPLICATIONS
985,970  3/1965  United Kingdom Primary Examiner—Sam Rosen
Attorney, Agent, or Firm—William G. Jameson; Sidney B. Williams, Jr.; Roman Saliwanchik

[57] ABSTRACT

A method and therapeutic compositions for inducing interferon formation in vivo. To a host is administered an interferon inducer selected from the group consisting of
 a. 1,5-bis[(3-morpholinopropyl)amino]anthraquinone,
 b. 1-[(2-aminoethyl)amino]-5-[[1-(hydroxymethyl)-propyl]amino]anthraquinone including primary -N-acylates, O-acylates, and O,primary-N-diacylates thereof, wherein the acylates are the acyl moiety of a carboxylic acid having from 2 to 18 carbon atoms, inclusive,
 c. 1,5-bis[[2-(diethylamino)ethyl]amino]anthraquinone,
 d. 1,5-bis[[3-(diethylamino)propyl]amino]anthraquinone,
 e. 1,5-bis[(3-piperidinopropyl)amino]anthraquinone.

22 Claims, No Drawings

INTERFERON INDUCTION

CROSS REFERENCE TO RELATED APPLICATIONS

This application is a continuation-in-part of application Ser. No. 500,052, filed Aug. 23, 1974, now abandoned.

BACKGROUND OF THE INVENTION

Interferon is the name given to certain protein molecules which appear in the blood or organs of animals, or in the medium of tissue cultures when such are exposed to an interferon inducer. Interferons are helpful in preventing or mitigating viral diseases. In seeking effective ways to induce interferon formation, numerous investigations have been directed to agents and methods to induce interferon formation. Such agents, which lead to the appearance of interferon in the blood or organs of animals, or in the medium of tissue cultures are designated as interferon inducers.

During the past decade a large number of agents have been tested as interferon inducers. Numerous interferon inducers have been reported, including various live or killed viruses, endotoxin, phytohaemagglutinin (PHA), bacteria, trachoma, mycoplasmas, protozoa, rickettsiae, nucleic acids, synthetic polymers, mitogens, polysaccharides, antibiotics, and tilorone hydrochloride, see Finter, *Interferons and Interferon Inducers* (1973).

Great Britain Patent 985,970 discloses compounds within the scope of the subject application as active against infections of *Hymenolepis nand* and *Oöchocistica symmeteria* in mice.

BRIEF SUMMARY OF THE INVENTION

This invention relates to new therapeutic compositions and to methods for using same for inducing interferon formation. According to the present invention, an active ingredient is administered to humans or interferon producing animals at doses effective for inducing interferon formation. The active ingredients of this invention consist of compounds selected from the group consisting of a. 1,5-bis[(3-morpholinopropyl)amino]anthraquinone, b. 1-[(2-aminoethyl)amino]-5-[[1-(hydroxymethyl)propyl]amino]anthraquinone including primary-N-acylates, O-acylates, and O,primary-N-diacylates thereof, wherein the acylates are the acyl moiety of a carboxylic acid having from two to eighteen carbon atoms, inclusive, c. 1,5-bis[[2-(diethylamino)ethyl]amino]anthraquinone, d. 1,5-bis[[3-(diethylamino)propyl]amino]anthraquinone, and e. 1,5-bis[(3-piperidinopropyl)amino]anthraquinone; or the pharmacologically acceptable acid addition salts thereof, in association with a pharmaceutical carrier.

DETAILED DESCRIPTION OF THE INVENTION

This invention relates to new pharmaceutical compositions and a method for inducing interferon formation in vivo. More particularly, this invention relates to pharmaceutical compositions having interferon inducing properties and the method of using said compositions.

The present invention comprises the compositions and the method of inducing interferon formation by administration of a compound selected from the group consisting of a. 1,5-bis[(3-morpholinopropyl)amino]anthraquinone, b. 1-[(2-aminoethyl)amino]-5-[[1-(hydroxymethyl)propyl]amino]anthraquinone including primary-N-acylates, O-acylates, and O,primary-N-diacylates thereof, wherein the acylates are the acyl moiety of a carboxylic acid having from 2 to 18 carbon atoms, inclusive.

c. 1,5-bis[[2-(diethylamino)ethyl]amino]anthraquinone, d. 1,5-bis[[3-(diethylamino)propyl]amino]anthraquinone, and e. 1,5-bis[(3-piperidinopropyl)amino]anthraquinone; or the pharmacologically acceptable acid addition salts thereof; in association with a pharmaceutical carrier.

Examples of carboxylic acids providing the acyl moiety of the acylates described above are aromatic carboxylic acids and saturated and unsaturated, straight or branched chain aliphatic carboxylic acids, for example, benzoic, acetic, propionic, butyric, isobutryic, tert-butylacetic, valeric, isovaleric, caproic, caprylic, decanoic, dodecanoic, lauric, tridecanoic, myristic, pentadecanoic, palmitic, margaric, stearic, undecylenic, oleic, hexynoic, heptynoic, and octynoic acids and the like.

Suitable pharmacologically acceptable acid addition salts include the hydrochloride, sulfate, phosphate, nitrate, citrate, acetate, lactate, succinate, and the like. These salts can be used in the same manner as the base compounds.

According to the present invention, the induction of interferon formation in vivo is achieved by administering the compounds of this invention as described above, hereinafter referred to as active ingredients, to a suitable host. By 'host' is meant certain interferon producing animals, i.e., certain intact viable animals which are capable of interferon production. The interferon producing animals contemplated are animals selected from the group consisting of humans, bovine, pigs, horses, sheep, mink, and fowl. A sub-generic scope of interferon producing animals contemplated as a part of this invention are animals selected from the group consisting of humans, bovine, pigs, and horses. Humans are contemplated as the ultimate interferon producing animal.

An embodiment of the subject invention is the administration of the compounds of this invention to a suitable tapeworm-free host, i.e., an interferon producing animal as described above free of tapeworm infections.

The mode of administration can be parenterally such as subcutaneously, intramuscularly, intradermally, intraperitoneally, intravenously or locally, preferably on a mucous membrane such as intranasally, pharyngolaryngeally, bronchially, bronchiolially, intravaginally, rectally or ocularly. The mode of administration can also be by implantation. Alternatively or concurrently, administration can be by the oral route, a preferred mode of administration for an interferon inducer. Practically, it is advantageous to administer the active ingredient to the host orally, intranasally, subcutaneously or intramuscularly.

The induction of interferon by administration of an active ingredient is demonstrated by established interferon assay methods such as plaque-reduction, see Finter, *Interferons and Interferon Inducers*, (1973). The interferon induced by the administration of an active ingredient can also be demonstrated by the protection of the host animals as well as tissue cultures against virus challenge.

The induction of interferon formation by the administration of an active ingredient of this invention has been demonstrated using established interferon plaque-reduction assay procedures as described above. For example, the induction of interferon formation by the administration of 1,5-bis[(3-morpholinopropyl)amino]anthraquinone has been demonstrated in mice using said established interferon plaque-reduction assay procedures.

Test results have shown 1,5-bis[(3-morpholinopropyl)amino]anthraquinone has not induced measurable interferon levels in rabbit following the oral administration of 1000 mg./kg. of said compound in a suitable vehicle.

Test results have shown 1,5-bis[(3-morpholinopropyl)amino]anthraquinone has not induced measurable levels in cat at 125 mg./kg., in dog at 125 mg./kg. and in monkey at 125 mg./kg. following the oral administration of the compound solubilized with hydrochloric acid in a suitable vehicle.

Test results have shown 1,5-bis[[3-(diethylamino)propyl]amino]anthraquinone hydrochloride has not induced measurable interferon levels in cat at 50 mg.kg., in dog at 75 mg./kg. and in monkey at 125, 100 and 75 mg./kg. following the oral administration of the compound in a suitable vehicle. A marginal level of interferon may have been seen in serum from a cat treated orally with 50 mg./kg. of 1,5-bis[[3-(diethylamino)propyl]amino]anthraquinone hydrochloride, however on retesting no measurable interferon level has been observed.

Test results have shown 1,5-bis[[2-diethylamino)ethyl]amino]anthraquinone has not induced measurable interferon levels in cat at 125 mg./kg., in dog at 125 mg./kg. and in monkey at 125, 100 and 75 mg./kg. following the oral administration of the compound solubilized with hydrochloric acid in a suitable vehicle.

Test results have shown, 1,5-bis[(3-piperidinopropyl)amino]anthraquinone has not induced measurable interferon levels in cat at 125 mg./kg., in dog at 125 mg./kg. and in monkey at 125 mg./kg. following the oral administration of the compound solubilized with hydrochloric acid in a suitable vehicle.

The daily dosage administered will be dependent upon the level of interferon desired, the type of animal involved, its age, health, weight, kind of concurrent treatment, if any, and frequency of treatment. Illustratively, dosage levels of the administered active ingredients can be: intravenous, 0.1 to about 50 mg./kg.; intraperitoneal, 0.1 to about 250 mg./kg.; subcutaneous, 0.1 to about 250 mg./kg.; intramuscular, 0.1 to about 250 mg./kg.; orally, 0.5 to about 500 mg./kg. and preferably about 5 to 250 mg./kg.; intranasal instillation, 0.1 to about 50 mg./kg., and aerosol, 0.1 to about 50 mg./kg. of animal (body) weight.

Expressed in terms of concentration, an active ingredient can be present in the compositions of the present invention for localized use about the cutis, intranasally, pharyngolaryngeally, bronchially, bronchiolially, intravaginally, rectally, or ocularly in a concentration of from about 0.1 to about 25% w/w of the composition, preferably about 1 to about 5% w/w of the composition; and for parenteral use in a concentration of from about 5.0 to about 50% w/v of the composition and preferably from about 10 to about 30% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage form can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil.

Tablets are made by preparing a powder mixture, granulating or slugging, adding a lubricant and pressing into tablets. The powder mixture is prepared by mixing an active ingredient, suitably communited, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and a polish coating of carnauba wax.

An active ingredient can also be presented in the undiluted pure form for use locally about the cutis, intranasally, pharyngolaryngeally, bronchially, bronchiolially or orally.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampul and sealing. Advantageously, adjuvants such as a local anesthetic, preservative and buffering agents can be dissolved in the vehicle. Parenteral suspensions are prepared in substantially the same mmanner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal route can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred.

The active ingredients can also be admixed in animal feed. The active ingredients can conveniently be prepared in the form of a food premix. The food premix can comprise an active ingredient in admixture with an edible pharmaceutical diluent such as starch, oatmeal, flour, calcium carbonate, talc, dried fish meal and the like non-toxic, orally acceptable pharmaceutical diluents. The prepared premix is then conveniently added to the regular feed.

For use as aerosols the active ingredients can be packaged in a pressurized aerosol container together with a gaseous or liquefied propellant, for example, dichlorodifluoromethane, carbon dioxide, nitrogen, propane and the like, with the usual adjuvants such as co-solvents and wetting agents as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredients to be employed as interferon inducers can be easily prepared by established procedures. Thus, the 1,5-bis substituted anthraquinones can be made according to procedures described by M. Ichikawa and M. Okazaki, Kogyo Kagaku Zasshi 67(1), 142-5(1964); Belgian Pat. No. 639,298; British Pat. No. 985,970; Netherlands Pat. No. 6,608,876 (Dec. 29, 1966; see Chemical Abstracts 67, 65436 page 6188 (1967)) and Netherlands Pat. No. 6,608,922 (Dec. 22, 1966; see Chemical Abstracts 67, 33837 page 3217 (1967)); and French Pat. No. 1,484,968. The non-bis-substituted 1,5-anthraquinone, 1-[(2-aminoethyl)amino]-5[[(1-hydroxymethyl)propyl]amino]-anthraquinone can be prepared according to methods known in the chemical synthesis art, for example, by reacting 1,5-diaminoanthraquinone with 1-hydroxy-2-chlorobutane, purifying the mono-substituted reaction product by known methods such as column chromatography, and subsequently reacting it with 1-chloro-2-aminoethane or aziridine.

Primary-N-acylates of 1-[(2-aminoethyl)amino]5[[(1-hydroxymethyl)propyl]amino]-anthraquinone can be prepared according to methods known in the chemical synthesis art, for example, by reacting 1-[(2-aminoethyl)amino]-5[[(1-hydroxymethyl)propyl]amino]-anthraquinone with one mole of an acylating agent, for example, an acyl halide or acyl anhydride, and purifying the reaction product by known methods such as column chromatography. The primary amino and the primary hydroxyl groups of 1-[(2-aminoethyl)amino]-5]](1-hydroxymethyl)-propyl]amino]-anthraquinone can be acylated simultaneously by use of two to three moles of acylating reagent and purification, according to the art. Primary-O-acylates of 1-[(2-aminoethyl)amino]-5[[(1-hydroxymethyl)propyl]amino]-anthraquinone can be prepared according to the art by first protecting the primary amino group with a suitable protective group, for example, a carbobenzoxy group, purifying the intermediate product, then reacting with one mole of acylating agent, purifying, and removing the protective group. Mixed O,primary-N-diacylates are made by combining the above methods.

The following examples are illustrative of the best mode contemplated by the inventors for carrying out their invention and are not to be construed as limiting.

EXAMPLE 1 Hard Gelatin Capsules

One thousand two-piece hard gelatin capsules for oral use, each capsule containing 100 mg. of 1,5-bis[(3-morpholinopropyl)amino]-anthraquinone are prepared from the following types and amounts of ingredients:

| | |
|---|---|
| 1,5-bis[(3-morpholinopropyl)-amino]-anthraquinone, micronized | 100 Gm. |
| Lactose | 100 Gm. |
| Corn starch | 20 Gm. |
| Talc | 20 Gm. |
| Magnesium stearate | 2 Gm. |

The 1,5-bis[(3-morpholinopropyl)amino]-anthraquinone, finely divided by means of an air micronizer, is added to the other finely powdered ingredients, mixed thoroughly and then encapsulated in the usual manner.

The foregoing capsules are useful for inducing interferon formation by the oral administration of one or two capsules one to four times a day to an adult human.

Using the procedure above, capsules are similarly prepared containing 1,5-bis[(3-morpholinopropyl- )amino]anthraquinone in 25, 50, 250, and 500 mg. amounts by substituting 25, 50, 250 and 500 Gm. of 1,5-bis[(3-morpholinopropyl)amino]-anthraquinone for the 100 Gm. used above.

EXAMPLE 2 Soft Gelatin Capsules

One-piece soft gelatin capsules for oral use, each containing 250 mg. of 1,5-bis[(3-morpholinopropyl)-amino]-anthraquinone (finely divided by means of an air micronizer), are prepared by first suspending the compound in 0.5 ml. of corn oil to render the material capsulatable and then capsulating in the above manner.

The foregoing capsules are useful for inducing interferon formation by the oral administration of one or two capsules one to four times a day to an adult human.

EXAMPLE 3 Tablets

One thousand tablets, each containing 500 mg. of 1,5-bis[(3-morpholinopropyl)amino]-anthraquinone are prepared from the following types and amounts of ingredients:

| | |
|---|---|
| 1,5-bis[(3-morpholinopropyl)-amino]-anthraquinone | 500 Gm. |
| Lactose | 75 Gm. |
| Corn starch | 50 Gm. |
| Magnesium stearate | 4 Gm. |
| Light liquid petrolatum | 5 Gm. |

The 1,5-bis[(3-morpholinopropyl)amino]-anthraquinone, finely divided by means of an air micronizer, is added to the other ingredients and then thoroughly mixed and slugged. The slugs are broken down by forcing through a Number Sixteen screen. The resulting granules are then compressed into tablets, each tablet containing 500 mg. of 1,5-bis[(3-morpholinopropyl)amino]-anthraquinone.

The foregoing tablets are useful for inducing interferon formation by the oral administration of one or two tablets one to four times a day to an adult human.

Using the procedure above, tablets are similarly prepared containing 1,5-bis[(3-morpholinopropyl)amino]-anthraquinone in 250 mg. and 100 mg. amounts by substituting 250 Gm. and 100 Gm. of 1,5-bis[(3-morpholinopropyl)amino]-anthraquinone for the 500 Gm. used above.

Using the procedure above, a bolus is similarly prepared containing 1,5-bis[(3-morpholinopropyl)amino]anthraquinone in the amount of 5000 mg. by substituting ten times the amounts of the ingredients used above. The bolus so prepared is useful for inducing interferon formation by the oral administration of 1 or 2 boli to a calf of 300 lbs.

EXAMPLE 4 Oral Suspension

One thousand ml. of an aqueous suspension for oral use, containing in each teaspoonful (5 ml.) dose, 500 mg. of 1,5-bis[(3-morpholinopropyl)amino]-anthraquinone, is prepared from the following types and amounts of ingredients:

| | |
|---|---|
| 1,5-bis[(3-morpholinopropyl)-amino]-anthraquinone micronized | 100 Gm. |
| Citric acid | 2 Gm. |
| Benzoic acid | 1 Gm. |
| Sucrose | 700 Gm. |
| Tragacanth | 5 Gm. |
| Lemon oil | 2 Gm. |
| Deionized water, q.s. | 1000 ml. |

The citric acid, benzoic acid, sucrose, tragacanth and lemon oil are dispersed in sufficient water to make 850 ml. of solution. The 1,5-bis[(3-morpholinopropyl)amino]-anthraquinone, finely divided by means of an air micronizer, is stirred into the syrup until uniformly distributed. Sufficient water is added to make 1000 ml.

The composition so prepared is useful for inducing interferon formation at a dose of one tablespoonful (15 ml.) three times a day to an adult human.

EXAMPLE 5

A sterile aqueous suspension for parenteral injection, containing in 1 ml. 300 mg. of 1,5-bis[(3-morpholinopropyl)amino]-anthraquinone is prepared from the following types and amounts of ingredients:

| | | |
|---|---|---|
| 1,5-bis[(3-morpholinopropyl)-amino]-anthraquinone, micronized | 300 | Gm. |
| Polysorbate 80 | 5 | Gm. |
| Methylparaben | 2.5 | Gm. |
| Propylparaben | 0.17 | Gm. |
| Water for injection q.s. 1000 ml. | | |

All the ingredients, except the 1,5-bis[(3-morpholinopropyl)amino]-anthraquinone, are dissolved in the water and the solution is sterilized by filtration. To the sterile solution is added the sterilized 1,5-bis[(3-morpholinopropyl)amino]-anthraquinone, finely divided by means of an air micronizer, and the final suspension is filled into sterile vials and the vials sealed.

The composition so prepared is useful for inducing interferon formation by the intramuscular administration of 0.3 to 0.5 ml. to an adult human.

EXAMPLE 6 Suppository, Rectal

One thousand suppositories, each weighing 2.5 Gm. and containing 150 mg. of 1,5-bis[(3-morpholinopropyl)amino]-anthraquinone, are prepared from the following types and amounts of ingredients:

| | |
|---|---|
| 1,5-bis[(3-morpholinopropyl)-amino]-anthraquinone, micronized | 150 Gm. |
| Propylene Glycol | 150 Gm. |
| Polyethylene glycol, 4000 q.s. | 2,500 Gm. |

The 1,5-bis[(3-morpholinopropyl)amino]-anthraquinone is finely divided by means of an air micronizer and added to the propylene glycol and the mixture passed though a colloid mill until uniformly dispersed. The polyethylene glycol 4000 is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally for inducing interferon formation to an adult human one to four times a day.

EXAMPLE 7 Intranasal Suspension

One thousand ml. of a sterile aqueous suspension for intranasal instillation, containing in each ml. 150 mg. of 1,5-bis[(3-morpholinopropyl)amino]-anthraquinone, is prepared from the following types and amounts of ingredients:

| | | |
|---|---|---|
| 1,5-bis[(3-morpholinopropyl)-amino]-anthraquinone, micronized | 150 | Gm. |
| Polysorbate 80 | 5 | Gm. |
| Methylparaben | 2.5 | Gm. |
| Propylparaben | 0.17 | Gm. |
| Deionized water. q.s. 1000 ml. | | |

All the ingredients, except the 1,5-bis[(3-morpholinopropyl)amino]-anthraquinone, are dissolved in the water and the solution sterilized by filtration. To the sterile solution is added the sterilized 1,5-bis[(3-morpholinopropyl)amino]-anthraquinone, finely divided by means of an air micronizer, and the final suspension is aseptically filled into sterile containers.

The composition so prepared is useful for inducing interferon formation by the intranasal instillation of 0.2 to 0.5 ml. given one to four times per day to an adult human.

EXAMPLE 8 Animal Feed

One thousand grams of feed premix is prepared from the following types and amounts of ingredients:

| | |
|---|---|
| 1,5-bis[(3-morpholinopropyl)-amino]anthraquinone | 20 Gm. |
| Soybean meal | 400 Gm. |
| Fish meal | 400 Gm. |
| Wheat germ oil | 50 Gm. |
| Sorghum molasses | 130 Gm. |

The ingredients are mixed together and pressed into pellets.

The premix can be fed to laboratory animals directly, i.e., rats and mice, for induction of interferon formation.

For other animals the premix can be added to the regular feed of bovine, pigs, horses, sheep, mink or fowl in an amount calculated to give the desired dose of 1,5-bis[(3-morpholinopropyl)amino]anthraquinone. For example, premix can be added to an animal's regular feed to provide a desired dose of 200 mg./kg./day.

EXAMPLE 9 Powder

Five hundred grams of 1,5-bis[(3-morpholinopropyl)amino]anthraquinone in bulk form is finely divided by means of an air micronizer. The micronized powder is placed in a shaker-type container.

The foregoing composition is useful for inducing interferon formation at localized sites about the cutis by applying the powder one to four times per day to an adult human.

EXAMPLE 10 Oral Powder

One thousand grams of 1,5-bis[(3-morpholinopropyl)amino]-anthraquinone in bulk form is finely divided by means of an air micronizer. The micronized powder is divided into individual doses of 250 mg. and packaged.

The foregoing powders are useful for inducing interferon formation by the oral administration of one to two powders suspended in a glass of water one to four times per day to an adult human.

EXAMPLE 11 Insufflation

One thousand grams of 1,5-bis[(3-morpholinopropyl)amino]-anthraquinone in bulk form is finely divided by means of an air micronizer.

The foregoing composition is useful for inducing interferon formation by the inhalation of 30 to 75 mg. one to four times per day to an adult human.

EXAMPLE 12 Hard Gelatin Capsules

One thousand two-piece hard gelatin capsules for oral use, each capsule containing 100 mg. of 1,5-bis[(3-morpholinopropyl)amino]-anthraquinone, are prepared from 100 grams of 1,5-bis[(3-morpholinopropyl)amino]-anthraquinone.

The 1,5-bis[(3-morpholinopropyl)amino]-anthraquinone is finely divided by means of an air micronizer and encapsulated in the usual manner.

Using the procedure above, capsules are similarly prepared containing 1,5-bis[(3-morpholinopropyl)amino]anthraquinone in 25, 50, 250 and 500 mg. amounts by substituting 25, 50, 250 and 500 Gm. of 1,5-bis[(3-morpholinopropyl)amino]anthraquinone for the 100 Gm. used above.

The foregoing capsules are useful for inducing interferon formation by the oral administration of one or two capsules one to four times a day to an adult human.

EXAMPLE 13 Tablets

One thousand tablets, each containing 294 mg. of 1,5-bis[(3-morpholinopropyl)amino]anthraquinone are prepared from the following types and amounts of ingredients:

| | |
|---|---|
| 1,5-bis[(3-morpholinopropyl)-amino]anthraquinone | 294 Gm. |
| Magnesium stearate | 6 Gm. |

To the 1,5-bis[(3-morpholinopropyl)amino]anthraquinone, finely divided by means of an air micronizer, is added the magnesium stearate and then thoroughly mixed and slugged. The slugs are broken down by forcing through a Number 16 screen. The resulting granules are then compressed into tablets, each tablet containing 294 mg. of 1,5-bis[(3-morpholinopropyl)amino]anthraquinone.

EXAMPLE 14 Parenteral Preparation

A sterile aqueous preparation for intramuscular injection, containing in one ml. 50 mg. of 1,5-bis[(3-morpholinopropyl)amino]anthraquinone is prepared from the following types and amounts of ingredients:

| | | |
|---|---|---|
| 1,5-bis[(3-morpholinopropyl)-amino]anthraquinone, micronized | 50 | Gm. |
| Polysorbate 80 | 0.5 | Gm. |
| Water for injection q.s. | 1000 | ml. |

The polysorbate 80 is dissolved in water and the solution is sterilized by filtration. To the sterile solution is added the sterilized 1,5-bis[(3-morpholinopropyl)amino]anthraquinone, finely divided by means of an air micronizer, and the final solution is filled into sterile vials and the vials sealed.

The composition so prepared is useful for inducing interferon formation by the intramuscular administration of 1.0 ml. to a 10 kg. child.

EXAMPLE 15

Following the procedure of the preceding Examples 1 through 14, inclusive, compositions are prepared substituting equivalent amounts of the pharmacologically acceptable acid addition salts of 1,5-bis[(3-morpholino-propyl)-amino]-anthraquinone for the free base of the examples.

EXAMPLE 16

Following the procedure of the preceding Examples 1 through 14, inclusive, compositions are prepared substituting equivalent amounts of 1[(2-aminoethyl)amino]-5-[[(1-hydroxymethyl)propyl]amino]anthraquinone, 1-[(2-acetamidoethyl)amino]-5-[[1-(hydroxymethyl)propyl[amino]-anthraquinone, 1-[(2-palmitamidoethyl)amino]-5-[[1-(hydroxymethyl)propyl-[amino[-anthraquinone, 1-[(2-benzamidoethyl)amino[-5-[[1-(hydroxymethyl)propyl]amino]-anthraquinone, 1-[(2-aminoethyl)amino]-5-[[1-(acetoxymethyl)propyl]amino]-anthraquinone, 1-[(2-aminoethyl)amino]-5-[[1-(palmitoxymethyl)propyl]amino]-anthraquinone, 1-[(2-aminoethyl)amino]-5-[[1-(benzoxymethyl)propyl]amino]-anthraquinone, 1-[(2-acetamidoethyl)amino]-5-[[1-(acetoxymethyl)propyl]amino]-anthraquinone, 1-[(2-benzamidoethyl)amino]-5-[[1-(acetoxymethyl)propyl]amino]-anthraquinone, 1-[(2-acetamidoethyl)amino]-5-[[1-(palmitoxymethyl)propyl]amino]-anthraquinone, 1-[(2-benzamidoethyl)amino]-5-[[1-(benzoxymethyl)propyl]amino]-anthraquinone, 1,5-bis[[2-(diethylamino)propyl]amino]-anthraquinone, 1,5-bis[[3-(diethylamino)propyl]amino]-anthraquinone, 1,5-bis[(3-piperidinopropyl)amino]-anthraquinone or the pharmacologically acceptable addition salts of each of the foregoing compounds for 1,5-bis[(3-morpholino-propyl)amino]-anthraquinone of each of the examples to provide similar therapeutic properties.

I claim:

1. A method for inducing interferon formation in an interferon producing animal in need of such treatment selected from the group consisting of humans, bovine, pigs, horses, sheep, mink, and fowl which comprises administering to said animal an amount effective to induce interferon formation in said animal of a compound selected from the group consisting of
   a. 1,5-bis[(3-morpholinopropyl)amino]anthraquinone,
   b. 1-[(2-aminoethyl)amino]-5-[[1-(hydroxymethyl)propyl]amino]anthraquinone including primary-N-acylates, O-acylates, and O, primary-N-diacylates thereof, wherein the acylates are the acyl moiety of a carboxylic acid having from two to eighteen carbon atoms, inclusive,
   c. 1,5-bis[[2-(diethylamino)ethyl]amino]anthraquinone,
   d. 1,5-bis[[3-(diethylamino)propyl]amino]anthraquinone, and
   e. 1,5-bis[(3-piperidinopropyl)amino]anthraquinone; or the pharmacologically acceptable acid addition salts thereof.

2. A method for inducing interferon formation according to claim 1, wherein the compound is administered in association with a pharmaceutical carrier to the interferon producing animal in unit dosage form, from about 0.1 to about 500 milligrams of said compound per kilogram body weight of said animal.

3. A method for inducing interferon formation according to claim 2 wherein the compound is 1,5-bis[(3-morpholinopropyl)amino]anthraquinone or the pharmacologically acceptable acid addition salts thereof.

4. A method for inducing interferon formation according to claim 2, wherein the compound is 1-[(2-aminoethyl)amino]-5-[[1-(hydroxymethylpropyl-]amino]anthraquinone including primary-N-acylates, O-acylates, and O,primary-N-dicylates thereof, wherein the acylates are the acyl moiety of a carboxylic acid having from two to eighteen carbon atoms, inclusive.

5. A method for inducing interferon formation according to claim 2, wherein the compound is 1,5-bis[[2-diethylamino)ethyl]amino]anthraquinone or the pharmacologically acceptable acid addition salts thereof.

6. A method for inducing interferon formation according to claim 2, wherein the compound is 1,5-bis[[3-(diethylamino)propyl]amino]anthraquinone or the pharmacologically acceptable acid addition salts thereof.

7. A method for inducing interferon formation according to claim 2, wherein the compound is 1,5-bis[(3-piperidinopropyl)amino]anthraquinone or the pharmacologically acceptable acid addition salts thereof.

8. A method for inducing interferon formation in an interferon producing animal in need of such treatment selected from the group consisting of humans, bovine, pigs, and horses which comprises administering to said animal an amount effective to induce interferon formation in said human or animal of a compound selected from the group consisting of
   a. 1,5-bis[(3-morpholinopropyl)amino]anthraquinone,
   b. 1-[(2-aminoethyl)amino]-5-[[1-(hydroxymethyl)propyl]amino]anthraquinone including primary-N-acylates, O-acylates, and O,primary-N-diacylates thereof, wherein the acylates are the acyl moiety of a carboxylic acid having from two to eighteen carbon atoms, inclusive,
   c. 1,5-bis[[2-(diethylamino)ethyl]amino]anthraquinone,
   d. 1,5-bis[[3-(diethylamino)propyl]amino]anthraquinone, and
   e. 1,5-bis[(3-piperidinopropyl)amino]anthraquinone; or the pharmacologically acceptable acid addition salts thereof.

9. A method for inducing interferon formation according to claim 8, wherein the compound is administered in association with a pharmaceutical carrier to the interferon producing animal in unit dosage form, from about 0.1 to about 500 milligrams of said compound per kilogram body weight of said animal.

10. A method for inducing interferon formation according to claim 9, wherein the compound is 1,5-bis[(3-morpholinopropyl)amino]anthraquinone or the pharmacologically acceptable acid addition salts thereof.

11. A method for inducing interferon formation according to claim 9, wherein the compound is 1-[(2-aminoethyl)-amino]-5-[[1-(hydroxymethyl)propyl-]amino]anthraquinone including primary-N-acylates, O-acylates, and O,primary-N-diacylates thereof, wherein the acylates are the acyl moiety of a carboxylic acid having from two to eighteen carbon atoms, inclusive.

12. A method for inducing interferon formation according to claim 9, wherein the compound is 1,5-bis[[2-(diethylamino)ethyl]amino]anthraquinone or the pharmacologically acceptable acid addition salts thereof.

13. A method for inducing interferon formation according to claim 9, wherein the compound is 1,5-bis[[3-(diethylamino)propyl]amino]anthraquinone or the pharmacologically acceptable acid addition salts thereof.

14. A method for inducing interferon formation according to claim 9, wherein the compound is 1,5-bis[(3-piperidinopropyl)amino]anthraquinone or the pharmacologically acceptable acid addition salts thereof.

15. A method for inducing interferon formation in humans in need of such treatment which comprises administering to said human an amount effective to induce interferon formation in said human of a compound selected from the group consisting of
   a. 1,5-bis[(3-morpholinopropyl)amino]anthraquinone,
   b. 1-[(2-aminoethyl)amino]-5-[[1-(hydroxymethyl)propyl]amino]anthraquinone including primary-N-acylates, O-acylates, and O,primary-N-diacylates thereof, wherein the acylates are the acyl moiety of a carboxylic acid having from two to eighteen carbon atoms, inclusive,
   c. 1,5-bis[[2-(diethylamino)ethyl]amino]anthraquinone,
   d. 1,5-bis[[3-(diethylamino)propyl]amino]anthraquinone, and
   e. 1,5-bis[(3-piperidinopropyl)amino]anthraquinone; or the pharmacologically acceptable acid addition salts thereof.

16. A method for inducing interferon formation according to claim 15, wherein the compound is administered in association with a pharmaceutical carrier to the human in unit dosage form, from about 0.1 to about 500 milligrams of said compound per kilogram body weight of said human.

17. A method for inducing interferon formation according to claim 16, wherein the compound is 1,5-bis[(3-morpholinopropyl)amino]anthraquinone or the pharmacologically acceptable acid addition salts thereof.

18. A method for inducing interferon formation according to claim 16, wherein the compound is 1-[(2-aminoethyl)amino]-5-[[1-(hydroxymethyl)propyl]amino]anthraquinone including primary-N-acylates, O-acylates, and O,primary-N-diacylates thereof, wherein the acylates are the acyl moiety of a carboxylic acid having from two to eighteen carbon atoms, inclusive.

19. A method for inducing interferon formation according to claim 16, wherein the compound is 1,5-bis[[2-(diethylamino)ethyl]amino]anthraquinone or the pharmacologically acceptable acid addition salts thereof.

20. A method for inducing interferon formation according to claim 16, wherein the compound is 1,5-bis[[3-(diethylamino)propyl]amino]anthraquinone or the pharmacologically acceptable acid addition salts thereof.

21. A method for inducing interferon formation according to claim 16, wherein the compound is 1,5-bis[(3-piperidinopropyl)amino]anthraquinone or the pharmacologically acceptable acid addition salts thereof.

22. A sterile pharmaceutical composition for parenteral administration comprising from about 5.0 percent to about 50 percent, w/v, of a member selected from the group consisting of
   a. 1,5-bis[(3-morpholinopropyl)amino]anthraquinone,
   b. 1-[(2-aminoethyl)amino]-5-[[1-(hydroxymethyl)propyl]amino]anthraquinone including primary-N-acylates, O-acylates, and O,primary-N-diacylates thereof, wherein the acylates are the acyl moiety of a carboxylic acid having from 2 to 18 carbon atoms, inclusive,
   c. 1,5-bis[[2-(diethylamino)propyl]amino]anthraquinone,
   d. 1,5-bis[[3-(diethylamino)propyl]amino]anthraquinone, and
   e. 1,5-bis[(3-piperidinopropyl)amino]anthraquinone; or the pharmacologically acceptable acid addition salts thereof, in association with a pharmaceutical carrier.

* * * * *

UNITED STATES PATENT AND TRADEMARK OFFICE
CERTIFICATE OF CORRECTION

PATENT NO. : 4,027,021
DATED : May 31, 1977
INVENTOR(S) : Gerald E. Underwood

It is certified that error appears in the above—identified patent and that said Letters Patent is hereby corrected as shown below:

Column 2, line 25: "isobutryic" should read -- isobutyric --.
Column 3, lines 31-32: "50 mg.kg.," should read -- 50 mg./kg., --.
Column 5, line 12: "same mmanner" should read -- same manner --.
Column 6, lines 6-7: "(December 22, 1966;" should read -- (December 29, 1966; --.
Column 6, line 28: "amino]-5]](1-" should read -- amino]-5[[(1- --.

Column 11, line 21: "propyl[amino]" should read -- propyl]-amino] --.
Column 11, lines 22-23: "propyl[amino[" should read -- propyl]amino] --.
Column 12, line 11: "(hydroxymethylpropyl " should read -- (hydroxymethyl)-propyl --.

Signed and Sealed this

Fifteenth Day of September 1981

[SEAL]

Attest:

Attesting Officer

GERALD J. MOSSINGHOFF

Commissioner of Patents and Trademarks